United States Patent
Taylor et al.

(10) Patent No.: US 9,345,397 B2
(45) Date of Patent: May 24, 2016

(54) OPTICAL SENSING SYSTEM FOR COCHLEAR IMPLANT SURGERY

(75) Inventors: Russell H. Taylor, Severna Park, MD (US); Jin U. Kang, Ellicott City, MD (US); John Niparko, Glen Arm, MD (US)

(73) Assignee: The Johns Hopkins University, Baltimore, MD (US)

( * ) Notice: Subject to any disclaimer, the term of this patent is extended or adjusted under 35 U.S.C. 154(b) by 800 days.

(21) Appl. No.: 13/238,538

(22) Filed: Sep. 21, 2011

(65) Prior Publication Data

US 2012/0172893 A1 Jul. 5, 2012

Related U.S. Application Data

(60) Provisional application No. 61/384,934, filed on Sep. 21, 2010.

(51) Int. Cl.
| | | |
|---|---|---|
| *A61B 6/00* | (2006.01) | |
| *A61B 1/227* | (2006.01) | |
| *A61B 1/00* | (2006.01) | |
| *A61B 5/00* | (2006.01) | |
| *A61F 11/00* | (2006.01) | |
| *A61N 1/36* | (2006.01) | |

(52) U.S. Cl.
CPC ............ *A61B 1/227* (2013.01); *A61B 1/00172* (2013.01); *A61B 5/0066* (2013.01); *A61F 11/004* (2013.01); *A61N 1/36032* (2013.01)

(58) Field of Classification Search
CPC .. A61B 5/0066; A61B 5/6852; A61B 5/6867; A61B 5/6886; A61B 8/12; A61B 2019/5234; A61B 1/227; A61B 1/00172; A61M 2025/0166; A61M 25/0102; A61N 1/0541; A61N 1/36032; G01B 9/02091; A61F 11/004
USPC ............................ 600/424, 437–480; 606/130
See application file for complete search history.

(56) References Cited

U.S. PATENT DOCUMENTS

| | | |
|---|---|---|
| 4,532,930 A | 8/1985 | Crosby et al. |
| 5,803,898 A | 9/1998 | Bashour |
| 5,833,367 A | 11/1998 | Cheslock et al. |
| 6,119,044 A | 9/2000 | Kuzma |
| 6,149,657 A | 11/2000 | Kuzma |
| 6,163,729 A | 12/2000 | Kuzma |
| 6,361,489 B1 | 3/2002 | Tsai |
| 6,564,087 B1 | 5/2003 | Pitris et al. |
| 6,582,441 B1 | 6/2003 | He et al. |

(Continued)

OTHER PUBLICATIONS

Schurzig, D. et al., "A force sensing robot for cochlear electrode implantation", IEEE International Conference on Robotics and Automation, 2010, pp. 3674-3679.

(Continued)

*Primary Examiner* — Sanjay Cattungal
(74) *Attorney, Agent, or Firm* — Venable LLP; Henry J. Daley; Laura G. Remus

(57) ABSTRACT

A sensing system for implant surgery includes an insertion device for moving an implant into a narrow cavity in a patient's body. A sensor measures the distance from an end of the insertion device to anatomic surfaces at a distance from the end of the insertion device. An optical coherence tomography (OCT) system integrates the sensor and produces OCT images, which can be quantified to distance measurements. The system is particularly useful for cochlear implant surgery.

33 Claims, 3 Drawing Sheets

(56) References Cited

U.S. PATENT DOCUMENTS

| | | | |
|---|---|---|---|
| 7,050,858 B1 | 5/2006 | Kuzma et al. | |
| 7,841,719 B2* | 11/2010 | Podoleanu | A61B 3/102 351/212 |
| 8,010,210 B2* | 8/2011 | Rau et al. | 607/137 |
| 8,214,010 B2* | 7/2012 | Courtney | A61B 5/0062 600/109 |
| 8,380,288 B2* | 2/2013 | Labadie | A61B 5/06 600/407 |
| 8,460,195 B2* | 6/2013 | Courtney | A61B 5/0062 600/459 |
| 8,736,935 B2* | 5/2014 | Antkowiak | A61B 3/102 359/200.7 |
| 2006/0241342 A1* | 10/2006 | Macaulay | A61B 5/0066 600/104 |
| 2008/0170204 A1* | 7/2008 | Podoleanu | A61B 3/102 351/206 |
| 2009/0264768 A1* | 10/2009 | Courtney | A61B 5/0062 600/463 |
| 2009/0275818 A1* | 11/2009 | Rau | A61B 5/06 600/379 |
| 2010/0228119 A1* | 9/2010 | Brennan | A61B 5/0066 600/424 |
| 2010/0228123 A1* | 9/2010 | Brennan | A61B 5/0066 600/437 |
| 2010/0228124 A1* | 9/2010 | Brennan | A61B 5/0066 600/437 |
| 2010/0228132 A1* | 9/2010 | Brennan | A61B 5/0066 600/478 |
| 2010/0228238 A1* | 9/2010 | Brennan | A61B 5/0066 606/13 |
| 2010/0239126 A1* | 9/2010 | Grafenberg | A61B 5/6817 382/106 |
| 2011/0009752 A1* | 1/2011 | Chen | A61B 5/0066 600/478 |
| 2011/0066160 A1* | 3/2011 | Simaan | A61N 1/05 606/129 |
| 2013/0128267 A1* | 5/2013 | Kang | G01B 9/02074 356/326 |

OTHER PUBLICATIONS

Zhang, J. et al., "Path planning and workspace determination for robot-assisted insertion of steerable electrode arrays for cochlear implant surgery", Med Image Comput Comput Assist Interv, vol. 11—Pt 2, pp. 692-700, 2008.

Zhang, J. et al., "A pilot study of robot-assisted cochlear implant surgery using steerable electrode arrays", Med Image Comput Comput Assist Interv, vol. 9—Pt 1, pp. 33-40, 2006.

Zhang, J. et al., "Inroads Toward Robot-Assisted Cochlear Implant Surgery Using Steerable Electrode Arrays", Otologyand Neurotology, p. in Press; Published ahead of print, 2010 10.1097/ MAO. Ob013e3181e7117e.

Coulson, C. et al., "An autonomous surgical robot for drilling a cochleostomy: preliminary porcine trial", Clin Otolaryngol, vol. 33-4, pp. 343-347, Aug. 2008.

Majdani, O. et al., "Force measurement of insertion of cochlear implant electrode arrays in vitro:comparison of surgeon to automated insertion tool", Acta Oto-Laryngologica, vol. 130-1, pp. 31-36, Jan. 2010.

Coulson, C. et al., "ENT challenges at the small scale", Int J Med Robot, vol. 3-2, pp. 91-96, Jun. 2007.

Briggs, R. et al., "Development and evaluation of the modiolar research array—multi-centre collaborative study in human temporal bones", Cochlear Implants Int . Aug. 12, 2011(3) pp. 129-139, PMCID: PMC3159433).

International Search Report and Written Opinion received in PCT/US2011/052503 filed Sep. 21, 2011.

"Cochlear Implant," Wikipedia, 2010, http://en.wikipedia.org/wiki/Cochlear_Implant.

"Statistics about Hearing, Balance, Ear Infections, and Deafness," http://www.nidcd.nih.gov/health/statistics/hearing.asp#1,2010.

Ang et al., "An Active Hand-Held Instrument for Enhanced Microsurgical Accuracy", in *Medical Image Computing and Computer-Assisted Interventions MICCAI 2000*, Pittsburgh, 2000.

Balicki et al.,"Micro-force Sensing in Robot Assisted Membrane Peeling for Vitreoretinal Surgery", in Medical Image Computing and Computer-Assisted Intervention (M ICCAI),Beijing,Sep. 2010, p. to appear.

Balicki et al.,"Single Fiber Optical Coherence Tomography Microsurgical Instruments for Computer and Robot-Assisted Retinal Surgery", in Medical Image Computing and Computer Assisted Surgery (MICCAI 2009),London2009, pp. 108-115. PMID: Pending.

Berkelman et al., "Performance Evaluation of a Cooperative Manipulation Microsurgical Assistant Robot Applied to Stapedotomy", in *Medical Image Computing and Computer-Assisted Interventions (MICCAI 2001)*, Utrecht, 2001, pp. 1426-1429.

Choi et al., "Flexure-based manipulator for active handheld microsurgical instrument", in *Proc. 27th Annu. Intl. Conf IEEE Eng. Med. Biol. Soc*, Shanghai, China, 2005.

Das et al., "Evaluation of a telerobotic system to assist surgeons in microsurgery", *Computer Aided Surgery*, vol. 4-, pp. 1525, 1999.

Han et al., "Common-path Fourier-domain optical coherence tomography with a fiber optic probe integrated into a surgical needle", in Conference on Lasers and Electro-Optics (CLEO),Baltimore,May 31-Jun. 5, 2009, pp. 163-166.

Kang et al., "Fourier Domain common-path fiber OCT with tunable reference: analysis and optimization", *OSA Technical Digest, CLEO*, p. JtuA55, 2007.

Kang et al., "1-0 Surface Tracking and Motion Compensation Handheld Microsurgical Tool System based on dynamic Common-Path Optical Coherence Tomography Sensor", Report of invention No. C11161, Johns Hopkins University, Submitted Jul. 2010.

Kapoor et al., "Constrained Control for Surgical Assistant Robots", in *IEEE Int. Conference on Robotics and Automation*, Orlando, 2006, pp. 231236.

Kapoor, Motion Constrained Control of Robots for Dexterous Surgical Tasks, Ph.D. thesis in Computer Science, Johns Hopkins University, Baltimore, 2007.

Kumar et al., "An Augmentation System for Fine Manipulation", in *Medical Image Computing and Computer-Assisted Interventions (MICCAI)*, Pittsburgh, 2000, pp. 956-965.

Kumar et al., "Experiments with a Steady Hand Robot in Constrained Compliant Motion and Path Following", in *8th IEEE International Workshop on Robot and Human Interaction(R0-MAN)*, Pisa, Italy, 1999, pp. 92-97.

Kumar et al., "Performance of Robotic Augmentation in Microsurgery-Scale Motions", in *2nd Int. Symposium on Medical Image Computing and Computer-Assisted Surgery*, Cambridge, England, 1999, pp. 1108-1115.

Li et al., "Telerobot Control by Virtual Fixtures for Surgical Applications", in *Advances in Telerobotics Human Interfaces, Bilateral Control and Applications*, M. Ferre, M. Buss, R. Aracil, C. Melchiorri, and C. Balaguer, Eds., 2007, pp. 381-401.

Li et al., "A Constrained Optimization Approach to Virtual Fixtures", in *IEEE/RS] Int Conf on Intelligent Robots and Systems (IROS)*, Edmonton, Alberta, Canada, 2005, pp. 2924-2929.

Iordachita et al., "Steady-Hand Manipulator for Retinal Surgery", in MICCAI Workshop on Medical; Robotics, Copenhagen, 2006, pp. 66-73.

MacLachlan et al., "Compensation of tremor by an active handheld micromanipulator", *IEEE Trans Biomed Eng*, vol. in review-, 2007.

Rau et al., "Automated insertion of preformed cochlear implant electrodes: evaluation of curling behaviour and insertion forces on an artificial cochlear model", Int. Comput Assist Radiol Surg, vol. 5-2, pp. 173-181, Mar. 2010.

Riviere et al., "Toward active tremor canceling in handheld microsurgical instruments", *IEEE Trans Rob Autom*, vol. 19-5, pp. 793-800, 2003.

Rothbaum et al., "Task Performance in stapedotomy: Comparison between surgeons of different experience levels", *Otolaryngology—Head and Neck Surgery*, vol. 128-1, pp. 71-77, Jan. 2003.

Rothbaum et al., "Robot-assisted stapedotomy: micropick fenestration of the stapes footplate", *Otolaryngology—Head and Neck Surgery*, vol. 127-5, pp. 417-426, Nov. 2002.

(56) References Cited

OTHER PUBLICATIONS

Salcudean et al., "Performance Measurement in Scaled Teleoperation for Microsurgery", in *Proc. First Joint Conference of CVRMed and MRCAS*, Grenoble, France, 1997, pp. 789-798.

Schenker et al., "Development of a Telemantpulator for Dexterity Enhanced Microsurgery.", in *Proc. 2nd Int. Symp. on Medical Robotics and Computer Assisted Surgery*, Baltimore, Md., 1995, pp. 81-88.

Taylor et al., "A Steady-Hand Robotic System for Microsurgical Augmentation", International journal of Robotics Research, vol. 18-12, pp. 1201¬ 1210, 1999.

Uneri et al., "A STeady-Hand Eye Robot with Microforce Sensing for Vitreoretinal Surgery", IEEE RAS EMBS Int Conf Biomed Robot Biomechatron, Sep. 1, 2010; 2010 (26-29); 814-819.

Zhang et al., "In OSA CLEO/IQEC 2010," A; Free-Hand Surface Tracking and Motion Compensation Microsurgical Tool System based on Common-path Optical Coherence Tomography Distance Sensor, in OSA CLEO/IQEC,2010.

Zhang et al., "A surface topology and motion compensation system for microsurgery guidance and intervention based on common-path optical coherence tomography", IEEE Transactions on Biomedical Engineering, vol. 56-, pp. 2318-2311, 2009.

\* cited by examiner

OPTICAL SENSING SYSTEM FOR COCHLEAR IMPLANT SURGERY

REFERENCE TO RELATED APPLICATIONS

This application claims the benefit of U.S. Provisional Patent Application No. 61/384,934, filed on Sep. 21, 2010, which is hereby incorporated by reference for all purposes as if fully set forth herein.

FIELD OF THE INVENTION

The present invention pertains to an optical sensing system and method for implant surgery. More particularly, the present invention pertains to a sensing system and method for preventing damage to the cochlear during cochlear implant surgery.

BACKGROUND OF THE INVENTION

Cochlear implant surgery can be an immense auditory, linguistic and developmental benefit to patients with severe hearing deficiencies due to the loss of hair cell transduction within the cochlea. The surgical procedure is potentially complicated by difficulties with implanting electrode array insertion, and serious complications may occur.

One particularly challenging step is the actual insertion of the implant into the cochlea. After accessing the scala tympani (via direct round window insertion, or drilling open a cochleostomry to gain access to the cochlea), an electrode array is inserted into scala tympani of the cochlea. Several designs of cochlear implant arrays have relied on stylet-based insertion techniques.

Over the past 6 years, the Cochlear Corporation Freedom and C512 arrays have used a stylet-based strategy. In particular, a stylet is used to hold the implant straight while it is inserted to a desired depth into the cochlea. The array is advanced over the stylet, which is held in a fixed position. The implant naturally curves to follow the cochlea. The stylet is then withdrawn. If the stylet and implant are advanced too far into the cochlea, the resulting contact forces can damage the cochlea. There is also research to replace the stylet with a sheath around the electrode array to hold it straight while the implant is inserted down the cochlear canal. One example of such a sheath is the Modiolar Research Array (R. Briggs et al., "Development and evaluation of the modular research array—multi-centre collaborative study in human temporal bones", Cochlear Implants Int. 2011 Aug. 12 (3) pp. 129-139, PMCID: PMC3159433).

Several approaches to providing guidance or assistance in avoiding damage to the cochlea during implant insertion have been reported recently. In particular, Schurzig, Labadie, and Webster report a system that combines an "active cannula" robot with delicate force sensing capabilities to sense contact between the implant and the cochlea, using a force sensor incorporated into the robotic mechanism that advances the implant into the cochlea. D. Schurzig, R. F. Labadie, and R. J. Webster, "A force sensing robot for cochlear electrode implantation", in IEEE International Conference on Robotics and Automation, 2010, pp. 3674-3679. Rau et al. have also proposed a robotic cochlear insertion device and have reported phantom studies of insertion forces using a load cell attached to the insertion mechanism.

Zhang, Simaan, et al. have developed an actively deforming, steerable, cochlear implant that curves to follow the cochlea during insertion. See e.g., J. Zhang, W. Wei, S. Manolidis, J. T. Roland, Jr., and N. Simaan, "Path planning and workspace determination for robot-assisted insertion of steerable electrode arrays for cochlear implant surgery", Med Image Comput Comput Assist Interv, vol. 11-Pt 2, pp. 692-700, 2008; J. Zhang, K. Xu, N. Simaan, and S. Manolidis, "A pilot study of robot-assisted cochlear implant surgery using steerable electrode arrays", Med Image Comput Comput Assist Interv, vol. 9-Pt 1, pp. 33-40, 2006; J. Zhang, W. Wei, J. Ding, J. T. Roland, S. Manolidis, and N. Simaan, "Inroads Toward Robot-Assisted Cochlear Implant Surgery Using Steerable Electrode Arrays", Otology and Neurotology, p. in Press; Published ahead of print, 2010 10.1097/MAO.Ob013e3181e7117e. They report experiments using a load cell mounted on their robotic manipulation device. Some limitations of these systems include reliance on a fairly large and cumbersome robotic insertion tool and the necessity to implement an extremely delicate force sensing mechanism. In the case of the reported systems, the difficulty is exacerbated by the moving mass of the mechanism distal to the force sensor and possible friction forces.

Other authors have proposed robotic devices to assist in drilling the skull to gain access to the cochlea for implant insertion. These systems do not address the problem of inserting an implant without damage to the cochlea. See, e.g., C. J. Coulson, R. P. Taylor, A. P. Reid, M. V. Griffiths, D. W. Proops, and P. N. Brett, "An autonomous surgical robot for drilling a cochleostomy: preliminary porcine trial", Clin Otolaryngol, vol. 33-4, pp. 343-7, August 2008; and O. Majdani, D. Schurzig, A. Hussong, T. Rau, J. Wittkopf, T. Lenarz, and R. F. Labadie, "Force measurement of insertion of cochlear implant electrode arrays in vitro:comparison of surgeon to automated insertion tool", Acta Oto-Laryngologica, vol. 130-1, pp. 31-36, January 2010.

Skilled otologic surgeons have the manual dexterity and steadiness to insert implants without damage to the cochlea. What they lack is feedback to know when the implant or stylet has been introduced too far into the cochlea. See, e.g., C. J. Coulson, A. P. Reid, D. W. Proops, and P. N. Brett, "ENT challenges at the small scale", Int J Med Robot, vol. 3-2, pp. 91-6, June 2007.

Accordingly, there is a need in the art for a system that allows a surgeon to information regarding the location of the implant with respect to the cochlea walls.

SUMMARY

According to a first aspect of the present invention, a sensing system for implant surgery comprises an insertion device for moving an implant into a narrow cavity in a patient's body, and a sensor for measuring distance from an end of the insertion device to anatomic surfaces at a distance from the end of the insertion device.

According to a second aspect of the present invention, a sensing system for implant surgery comprises an implant adapted to be positioned into a narrow cavity during implant surgery, and a sensor for moving the implant into the narrow cavity and for measuring distance from an end of the sensor to anatomical surfaces at a distance from the end of the sensor.

According to a third aspect of the present invention, a method of implant surgery comprises providing an implant having a sensor disposed therein, moving the implant into a narrow cavity in a patient's body, measuring distance from an end of the sensor to anatomic surfaces at a distance from the end of the sensor, and measuring distance from an end of the sensor to anatomic surfaces at a distance from sides of the sensor or implant so as to center it from the cavity wall.

BRIEF DESCRIPTION OF THE DRAWINGS

The accompanying drawings provide visual representations which will be used to more fully describe the representative embodiments disclosed herein and can be used by those skilled in the art to better understand them and their inherent advantages. In these drawings, like reference numerals identify corresponding elements and.

DETAILED DESCRIPTION OF THE PREFERRED EMBODIMENTS

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

The present invention pertains to a sensing system for implant surgery. While the preferred embodiments describe a sensing system for use in cochlear implant surgery, it should be understood that present invention may be applied to other similar types of implant surgery, where an implant is placed into a narrow cavity in a patient's body.

Figure 1:
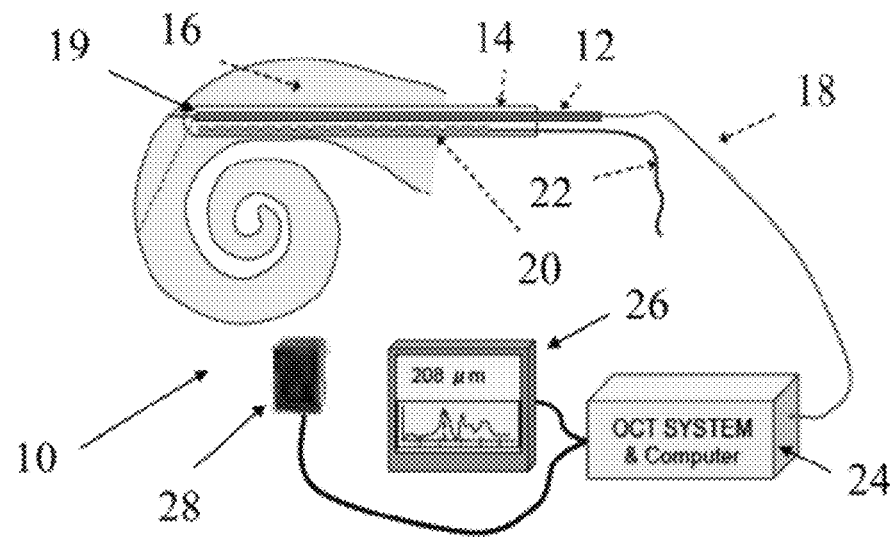
FIG. 1 illustrates a schematic of an exemplary system according to the features of the present invention.
Figure 2:
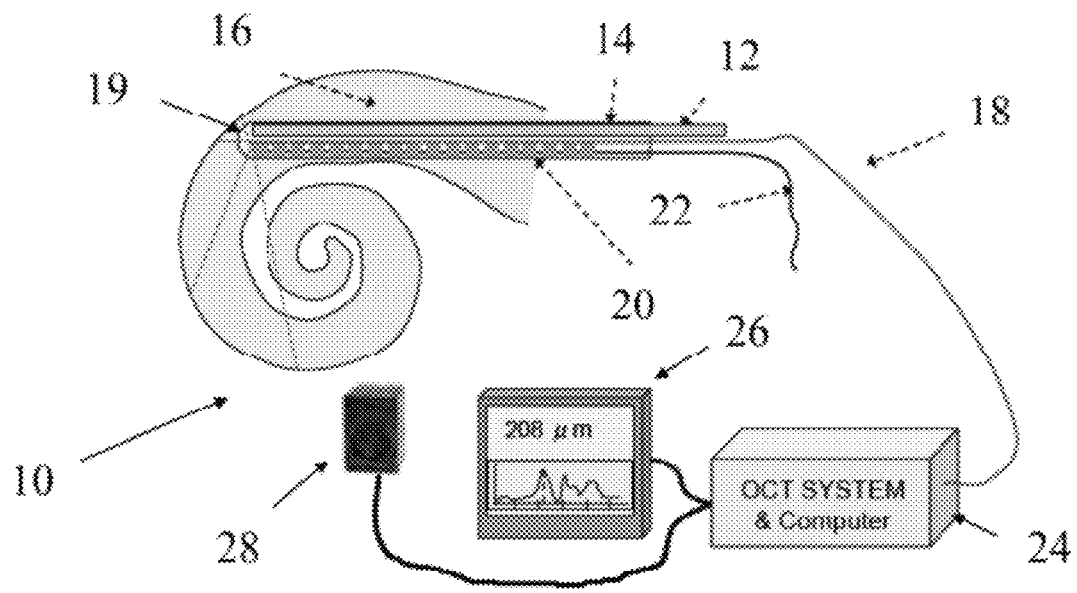
FIG. 2 illustrates a schematic of another exemplary system according to the features of the present invention.
Figure 3:
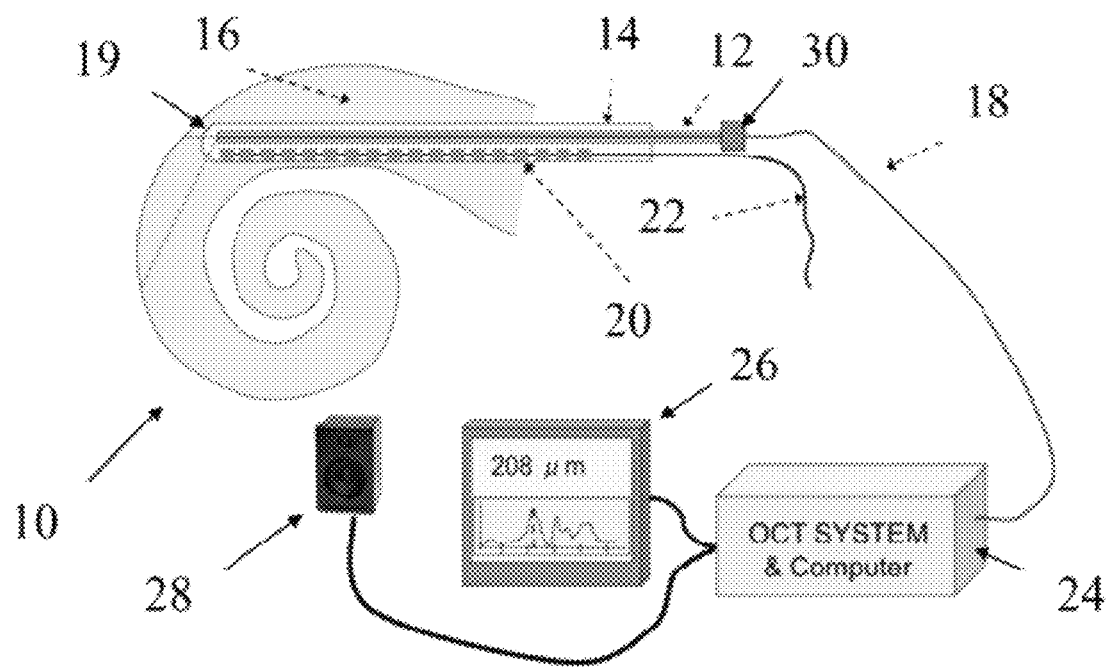
FIG. 3 illustrates a schematic of yet another exemplary system according to the features of the present invention.

With reference to FIGS. 1-3, the sensing system 10 includes an insertion device (or stylet) 12 for moving an implant 14 into a narrow cavity 16 in a patient's body. In the preferred embodiment, the implant 14 is a cochlear implant. In other embodiments (not shown), the insertion device 12 may be a sheath surrounding the implant 14. As is known in the art, a cochlear implant may be inserted into the hollow scala tympani of the cochlea of an ear. The cochlear implant includes an electrode array 20 with an electrode cable 22 that is connected to an implanted receiver and stimulator unit (not shown). The electrode array 20 receives processed signals, which are applied to the basilar membrane and the nerve cells within the cochlea, which causes the auditory nerve to be stimulated. A more detailed discussion of the components and operation of a cochlear implant device are described, for example, in U.S. Pat. No. 4,532,930, the entire disclosure of which is incorporated by reference herein.

During typical cochlear implant surgery, a stylet is used to move the implant into the scala tympani of the ear. A stylet is used to hold the implant straight while it is inserted into a desired depth into the cochlea. The array is advanced over the stylet, which is held in a fixed position. The implant is designed to naturally curve to follow the cochlea. The stylet is then withdrawn.

To better aid in determining how far to insert the implant, the sensing system 10 includes a sensor 18 for measuring the distance from a distal end 19 of the stylet or insertion device 12 to anatomic surfaces of the cavity 16 at a distance from the distal end 19 of the stylet 12. Any suitable design may be used for the insertion device or stylet itself. For example, the stylet might include a thin fiber optic probe surrounded by a metal or plastic sheath to provide strength and resistance to breaking. The sensor 18 may be integrated within the stylet 12 as shown in FIG. 1, or the sensor 18 may be disposed adjacent to the stylet 12, as shown in FIG. 2. Alternatively, the fiber optic probe may act as the stylet itself.

The sensor is preferably an optical sensor, and may comprise an optical waveguide to transmit and collect laser beam of light. Preferably, optical waveguide comprises an optical fiber. An optical fiber is preferred, as it can be manufactured in very small sizes and be flexible. For example, the fiber optic probe may be based on a standard communication grade optical fiber having a 125 micron diameter or smaller. The fiber end may be cleaved and polished perpendicular to the fiber or any angle between zero to 180 degrees to provide a forward or side looking beam. A large percentage of the fiber cladding can be removed without affecting the performance of the probe. This can be done chemically to reduce the fiber optic probe diameter to as small as approximately 50 microns.

With continued reference to FIGS. 1-3, the sensor 18 may be connected to an optical coherence tomography (OCT) system and computer 24. The distal end 19 of the sensor 18 provides a reference for the OCT distance sensor and emits one or more laser sensing beams to pass from the end and/or side through the implant 14 to the wall of the scala tympani, and back to monitor the position of the implant relative to the cochlea wall. Fiber couplers (not shown) route the light source from the OCT to the fiber probes and return signal to the OCT system. The reference signal is provided by the perpendicularly cleaved end of the fiber optic probe or similar reflecting point near the distal end of the fiber optic probe.

Preferably, the OCT system 24 is capable of providing at least "A-mode" OCT images of reflecting surfaces surrounding the stylet. Typically, the image may include the portion of the implant distal to the stylet and the interior surface of the scala tympani. Preferably, the OCT system is a Fourier domain common path OCT system (FD-CPOCT). A FD-CPOCT permits fast A-scan update rate with no mechanically moving parts. Furthermore, it permits the sensor to be disposable and allows a new sensor to be quickly attached. However, other OCT systems are possible, and within the scope of the invention.

The OCT system 24 includes a signal processor which may be a computer and is capable of processing OCT images produced by the OCT system 24 from the sensor to anatomic surfaces, and convert the OCT images to distances. Preferably, the insertion device 12 is positioned within the implant 14 at a known distance, typically less than 5 mm from the end of the implant. Since the distance from the distal end of the insertion device to the implant is known, the processor may compute the distance from the implant tip to the scala tympani wall.

Correct insertion of the implant 14 requires that the insertion device 12 be advanced until the tip of the implant 14 is at a predetermined distance (typically a few hundred microns) from the inner wall of the scala tympani, at a point just before it begins to curve around into its characteristic spiral shape.

The sensing system 12 and OCT system 24 allows for the distance to be sensed so that a surgeon is notified as to how much further to insert the implant.

As shown in FIGS. 1-3, the surgeon may be notified of this distance by displaying the distance on a visual display 26. The visual display 26 may be a computer graphical display showing the "A-mode" OCT image. For example, a graph of the intensity of the OCT signal against the distance from the end of the stylet or other reference may be displayed, as shown, for example, in FIG. 6. Alternatively, a computer graphical display of the processed distance information, such as a bar graph with graduated marks, in which the length of the bar is proportional to the processed distance, may be displayed. The distance may also be presented as a computer text display showing the distance in a particular unit, such as microns. The above displays may be used with additional graphical information showing the desired safe distance at which the surgeon should stop inserting. For example, this may be a simple line or reference mark on a bar graph or A-mode image display, but it may also be augmented by color information. For example, the display may be green when the insertion device is far from the wall, but may turn yellow when the insertion device is approaching the safety limit and red when the stylet is closer than the safety limit.

The distance may also be represented as auditory information on an auditory device 28, either in the form of spoken words or of tonal or other auditory signals. The auditory information may provide information about the distance to the wall or about distance relative to some safety limit. However, it should be understood that notification to the surgeon is not limited to the devices described above, but may be any interface system or method known in the art for providing information about the distance from the surgical tool to a surface or relative to a desired safety barrier, or any combination of systems and methods described above.

Figure 5:
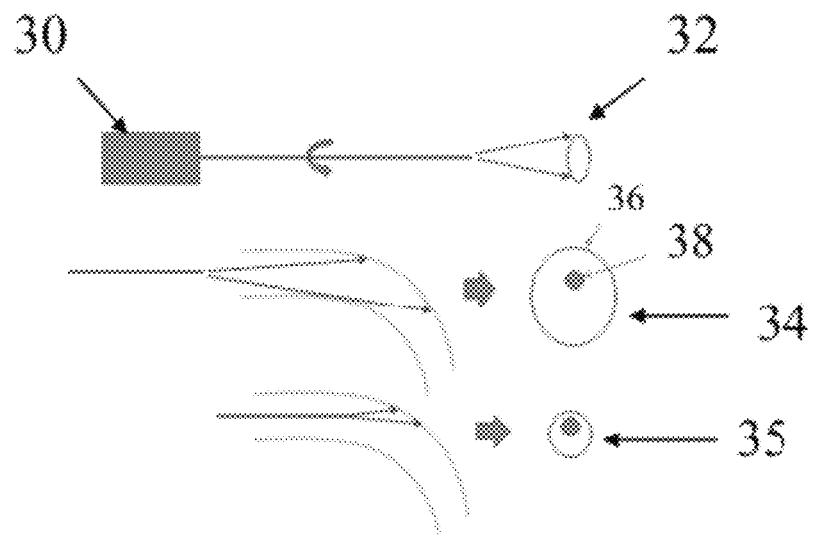
FIG. 5 illustrates exemplary fiber optic presentations according to features of the present invention.

With reference to FIGS. 3 and 5, the sensor 18 may be a small angle cone-bean scanning probe 30. With specific reference to FIG. 5, the scanning probe 30 spins about an axis forming an OCT scanning beam 32. A far polar image 34 and near polar image 35 may be formed, having a tissue boundary 36 and the fiber 38. These polar images can be combined to form a 3-dimensional image of the cochlear up to the first turn with quantitative dimensions of the cochlear.

As described above, the optical sensor may include facets for creating forward and side viewing probe beams so as to measure multiple distances. The beams can be used to constantly monitor both forward and side distances to the cochlear wall, and provide real-time sensing of the distances as the implant is being inserted. The multiple distances may be measured simultaneously or sequentially.

In addition, multiple sensors may be used to measure multiple distances between multiple anatomical locations. For example, one or more fibers may be used for this purpose. In one exemplary embodiment, three fiber probes may be bundled together—one forward looking and two side looking probes but orthogonal to each other. Three different distances would be determined and presented to the surgeon, to help the surgeon center the probes and prevent collision of the probes against the cochlear wall. In other embodiments, a bundle of optical fibers may be used to provide "B-mode" (cross-sectional) or "C-mode" (volumetry) images of the nearby anatomy. In still other embodiments, ultrasound sensors may be used to provide distances to anatomic surfaces or images of nearby anatomy. Such sensing configurations may be particularly well adapted to sheath-style insertion devices.

Preferably, the fibers are sufficiently strong so that they may bend with the implant without breaking Many such materials are known in the art, and the choice may be made depending on the specific optical and physical properties required. For example, a thinned optical fiber having 80 micron or less in diameter, with or without being coated with a polymer, is sufficiently flexible for this application. The sensor can be used to reshape the implant by manipulating its spatial relationship relative to the implant.

Figure 4:
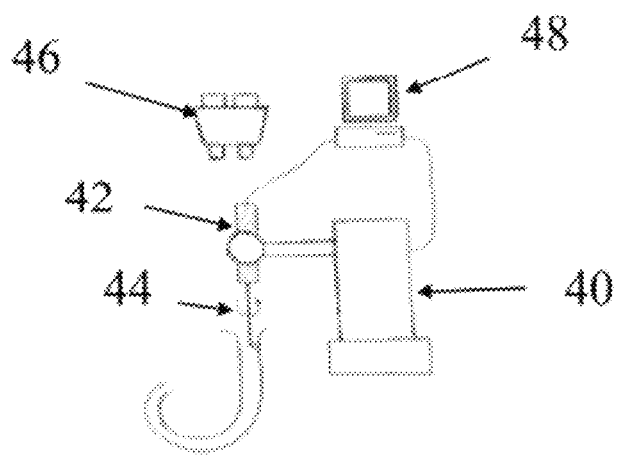
FIG. 4 illustrates a schematic of an exemplary system used in connection with a steady hand robot according to the features of the present invention.

Although the present invention is designed to be workable with conventional handheld instruments (e.g., cochlear implant jeweler's forceps and claws), it may also be used with robotic devices, such as Johns Hopkins Steady Hand robots, microsurgical tele-operation or high bandwidth handheld microsurgical systems. For example, with reference to FIG. 4, a steady hand robot 40 includes a tool holder 42 for holding the implant 44. A microscope 46 may be positioned above the patient for viewing by the surgeon. The surgeon may then manipulate the tool holder 42 and thereby move the implant into the cochlea of a patient. The OCT information may be sent back to an OCT system and computer 48 to be displayed thereon. The OCT distance information in these systems may either be used to provide feedback information to the surgeon, or may be incorporated into the robot control to enable the robot to maintain a desired stylet-to-wall distance or implement some other form of safety barrier, using methods known in the art.

EXAMPLE

The following Example has been included to provide guidance to one of ordinary skill in the art for practicing representative embodiments of the presently disclosed subject matter. In light of the present disclosure and the general level of skill in the art, those of skill can appreciate that the following Example is intended to be exemplary only and that numerous changes, modifications, and alterations can be employed without departing from the scope of the presently disclosed subject matter. The following Example is offered by way of illustration and not by way of limitation.

Figure 6:
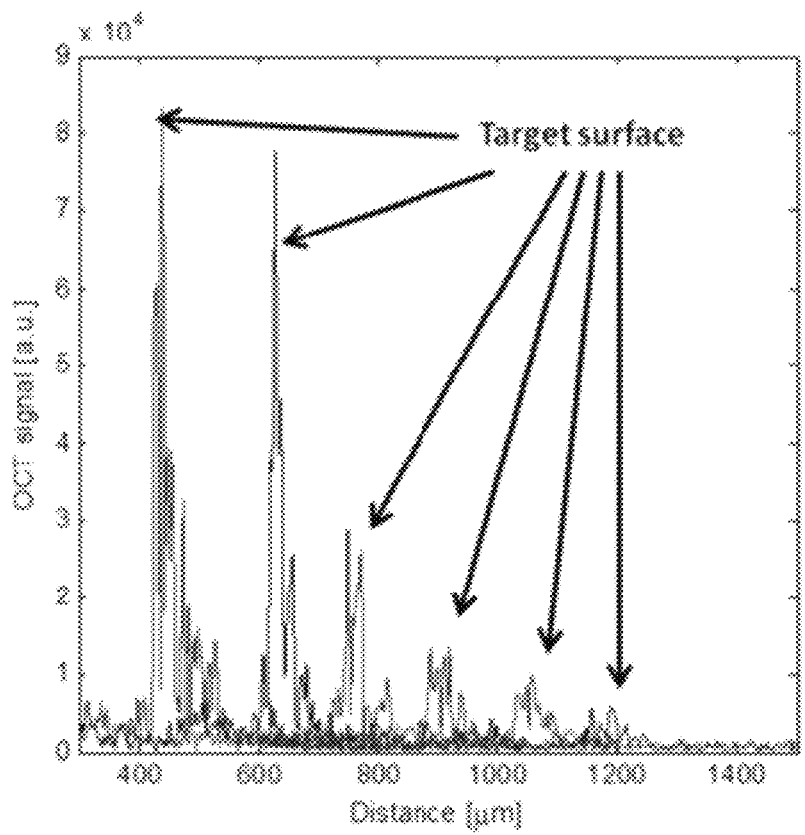
FIG. 6 is a graphical representation of OCT images as a function of distance according to features of the present invention.

A common-path fiber optic probe having 125 micron in diameter connected to a FD-CPOCT system was inserted into a cochlea on a cadaveric temporal bone for validation. In another experiment, a 125 micron fiber probe was inserted into a Cochlear Corp implant, replacing the stylet. The fiber/implant combination was inserted into a cochlea phantom. In both cases, the OCT probe was able to detect the wall of the cochlea as the probe/implant approached the turn. FIG. 6 shows the OCT A-mode signals as the implant approaches the target wall of the cochlea phantom. The A-mode signal was obtained at the rate of 70 KHz which allows the real-time continuous distance monitoring between the implant tip and the target wall.

Although the present invention has been described in connection with preferred embodiments thereof, it will be appreciated by those skilled in the art that additions, deletions, modifications, and substitutions not specifically described may be made without departing from the spirit and scope of the invention as defined in the appended claims.

The invention claimed is:
1. A sensing system for implant surgery, comprising:
an insertion device or stylet configured for moving a cochlear implant into a narrow cavity in a patient's body;
an optical sensor for measuring distance from an end of the insertion device to anatomic surfaces at a distance from the end of the insertion device; and
an optical coherence tomography (OCT) system connected to the optical sensor, wherein the optical sensor is incorporated within and at a distal end of the insertion device, and wherein a distal end of the optical sensor provides a reference signal for the OCT system.

2. The sensing system of claim 1, wherein the optical sensor comprises an optical waveguide to transmit and collect a laser beam of light.

3. The sensing system of claim 2, wherein the optical waveguide comprises an optical fiber.

4. The sensing system of claim 1, wherein the OCT system is a Fourier domain common path OCT (FD-CPOCT) system, and wherein the OCT system includes a computer processor for processing OCT images from the optical sensor to anatomic surfaces and converting the OCT images to distances.

5. The sensing system of claim 1, further comprising a display device for displaying OCT images or distance information to a surgeon.

6. The sensing system of claim 1, further comprising an auditory device for providing auditory information representing distance information.

7. The sensing system of claim 1, wherein said optical sensor includes facets for creating forward and side viewing probe beams so as to measure multiple distances.

8. The sensing system of claim 7, wherein the multiple distances are measured simultaneously.

9. The sensing system of claim 7, wherein the multiple distances are measured sequentially.

10. The sensing system of claim 1, further comprising multiple optical sensors to measure multiple distances between multiple anatomical locations.

11. The sensing system of claim 1, wherein the distance measurements are directed to a control system of a robotic device for cochlear implant surgery.

12. The sensing system of claim 1, wherein the optical sensor is an ultrasound sensor.

13. The sensing system of claim 1, wherein the insertion device is a stylet.

14. The sensing system of claim 1, wherein the insertion device is a sheath.

15. The sensing system of claim 14, wherein the optical sensor is an ultrasound sensor.

16. The sensing system of claim 1, wherein the OCT system produces A-mode OCT images.

17. The sensing system of claim 1, wherein the OCT system produces B-mode OCT images.

18. The sensing system of claim 1, wherein the OCT system produces C-mode OCT images.

19. A sensing system for implant surgery, comprising:
a cochlear implant adapted to be positioned into a narrow cavity during implant surgery;
an optical sensor for measuring distance from an end of the optical sensor to anatomical surfaces at a distance from the end of the optical sensor; and
an optical coherence tomography (OCT) system connected to the optical sensor,
wherein the optical sensor is incorporated within and at a distal end of the cochlear implant, and wherein a distal end of the optical sensor provides a reference signal for the OCT system.

20. The sensing system of claim 19, wherein the sensor is used to reshape the implant by manipulating its spatial relationship relative to the implant.

21. The sensing system of claim 19, further comprising one or more optical fibers disposed within the implant, said optical fibers configured to measure multiple distances including at least one of a forward distance and one or more side distances to a cavity wall.

22. The sensing system of claim 19, wherein the optical sensor comprises an optical waveguide to transmit and collect a laser beam of light.

23. The sensing system of claim 22, wherein the optical waveguide comprises an optical fiber.

24. The sensing system of claim 19, wherein said OCT system produces A-mode OCT images.

25. The sensing system of claim 19, wherein the OCT system is a Fourier domain common path OCT (FD-CPOCT) system, and wherein the OCT system includes a computer processor for processing OCT images from the optical sensor to anatomic surfaces and converting OCT images to distances.

26. The sensing system of claim 24, further comprising a display device for displaying OCT images or distance information to a surgeon.

27. The sensing system of claim 19, further comprising an auditory device for providing auditory information representing distance information.

28. The sensing system of claim 19, wherein said optical sensor includes facets for creating forward and side viewing probe beams so as to measure multiple distances.

29. The sensing system of claim 28, wherein the multiple distances are measured simultaneously.

30. The sensing system of claim 28, wherein the multiple distances are measured sequentially.

31. The sensing system of claim 19, wherein the distance measurements are directed to a control system of a robotic device for cochlear implant surgery.

32. A method of implant surgery, comprising:
providing a cochlear implant having an optical sensor integrated therein, wherein the optical sensor is integrated at a distal end of the cochlear implant;
providing an optical coherence tomography (OCT) system connected to the optical sensor, wherein a distal end of the optical sensor provides a reference signal for the OCT system;
moving the cochlear implant into a narrow cavity in a patient's body; and
measuring a distance from an end of the optical sensor to anatomic surfaces at a distance from the end of the optical sensor.

33. The method of claim 32, further comprising measuring a distance from an end of the optical sensor to anatomic surfaces at a distance from sides of the sensor or implant so as to center it from a cavity wall.

* * * * *